(12) United States Patent
Le Mouellic et al.

(10) Patent No.: US 6,638,768 B1
(45) Date of Patent: *Oct. 28, 2003

(54) PROCEDURE FOR SPECIFIC REPLACEMENT OF A COPY OF A GENE PRESENT IN THE RECIPIENT GENOME BY THE INTEGRATION OF A GENE DIFFERENT FROM THAT WHERE THE INTEGRATION IS MADE

(75) Inventors: Hervé Le Mouellic, Paris (FR); Philippe Brulet, Maurepas (FR)

(73) Assignee: Institut Pasteur, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 08/466,699

(22) Filed: Jun. 6, 1995

Related U.S. Application Data

(63) Continuation of application No. 08/301,037, filed on Sep. 6, 1994, now Pat. No. 6,528,313, which is a continuation of application No. 08/048,056, filed on Apr. 19, 1993, now abandoned, which is a continuation of application No. 07/598,679, filed as application No. PCT/FR90/00185 on Mar. 19, 1990, now abandoned.

(30) Foreign Application Priority Data

Mar. 20, 1989 (FR) ............................................ 89 03630

(51) Int. Cl.$^7$ .......................... C12N 5/16; C12N 15/64; C12N 15/63; C12N 15/11
(52) U.S. Cl. .................... 435/463; 435/461; 435/320.1; 536/23.1; 536/24.1
(58) Field of Search ............................ 435/172.3, 463, 435/461, 6, 91.2, 320.1, 354, 325; 536/23.1, 24.1

(56) References Cited

U.S. PATENT DOCUMENTS

| | | | |
|---|---|---|---|
| 5,272,071 A | 12/1993 | Chappel | 435/172.3 |
| 5,631,153 A | 5/1997 | Capecchi et al. | 435/172.3 |
| 5,641,670 A | 6/1997 | Treco et al. | 435/254.11 |
| 6,528,313 B1 | 3/2003 | Le Mouellic et al. | |
| 6,528,314 B1 | 3/2003 | Le Mouellic et al. | |

FOREIGN PATENT DOCUMENTS

| | | |
|---|---|---|
| EP | A 0074808 | 3/1983 |
| EP | A 0169672 | 1/1986 |
| EP | 0 247 494 | 12/1987 |
| EP | A 0279582 | 8/1988 |
| EP | A 0289121 | 11/1988 |
| EP | 0 452 484 | 11/1990 |
| WO | WO 91/06666 | 5/1991 |
| WO | WO 91/06667 | 5/1991 |

OTHER PUBLICATIONS

Letsou et al. Effect of the molecular nature of mutation on the efficiency of intrachromosomal gene conversion in mouse cells. Genetics vol. 117, pp. 759–769 (1987).*

Smithies et al. Insertion of DNA sequences into the human chromosomal beta–globin locus by homologous recombination. Nature vol. 317, pp. 230–234 (1985).*

Nagpal et al. Expression of the RAD1 and RAD3 genes of *Saccharomyces cerevisiae* is not affected by DNA damage or during the cell division cycle. Mol. Gen. Genet. vol. 199 pp. 59–63 (1985).*

Kim et al. Recombinant fagment assay for gene targeting based on the polymerase chain reaction. Nucleic Acids Res. vol. 16 pp. 8887–8903, 1988.*

Thomas et al. Site–Directed mutagenesis by gene targeting in mouse embryo–derived stem cells. Cell vol. 51 pp. 503–512, 1987.*

Jasin et al. Homologous integration in mammalian cells without target gene selection. Genes and Development vol. 2 pp. 1353–1363, 1988.*

Capecchi The new mouse genetics: Altering the genome by gene targeting. Trends in Genetics vol. 5 pp. 70–76, 1989.*

Capecchi, M.R., "The New Mouse Genetics: Altering te Genome by Gene Targeting," *Trends in Genetics* 5(3):70–76 (1989).

Doetschnman et al. Targeted mutation of the HPRT gene in mouse embryonic stem cells Proc. Natl. Acad. Sci. USA vol. 85 8583–8587, 1988.*

Zimmer et al. Production of chimaeric mice containing embryonic stem (ES) cells carrying a homeobox Hox 1.1 allele mutated by homologous recombination. Nature vol. 338 pp. 150–153, 1989.*

(List continued on next page.)

*Primary Examiner*—John S. Brusca
(74) *Attorney, Agent, or Firm*—Finnegan, Henderson, Farabow, Garrett & Dunner, L.L.P.

(57) ABSTRACT

The present invention relates to a process for targeted replacement of at least a part of an endogenous gene by at least a part of a foreign gene or targeted insertion of at least a part of a foreign gene at a targeted site in an endogenous gene in a cell by homologous recombination. This process includes (A) providing a vector which contains (1) at least a part of the foreign gene which is heterologous with respect to the endogenous gene, (2) a first flanking DNA sequence homologous to a first genomic sequence situated on one side of the part of the endogenous gene to be replaced or the targeted site; and (3) a second flanking DNA sequence homologous to a second genomic sequence situated on the other side of the part of the endogenous gene to be replaced or the targeted site, the foreign gene being located between the first and second flanking DNA sequences and is complementary to the part of the endogenous gene to be replaced; (B) transfecting a cell with the vector; (C) and selecting a transfected cell that contains the foreign gene at the targeted site or where the part of the endogenous gene is to be replaced. This invention also pertains to the vector, and the cell transfected by the vector.

44 Claims, 12 Drawing Sheets

OTHER PUBLICATIONS

Frohman et al.; Cut, Paste, and Save: New Approaches to Altering Specific Genes in Mice; Cell, vol. 56, pp. 145–147, Jan. 27, 1989.

Johnson et al.; Targeting of Nonexpressed Genes in Embryonic Stem Cells Via Homologous Recombination; Science, vol. 245, pp. 1234–1236, Sep. 1989.

Palmiter, R.D., et al., "Cell Lineage Ablation in Transgenic Mice by Cell–Specific Expression of a Toxin Gene," Cell 50: 435–443 (1987).

Yagi, T. et al, "Homologous recombination at c–fyn locus of mouse embryonic stem cells with use of diptheria toxin A–fragment gene in negative selection", Proc. Natl. Acad. Sci. USA. 87: 9918–9922 (1990).

Le Mouellic, H., et al., "Targeted replacement of the homeobox gene Hox–3.1 by the *Escherichia coli* lacZ in mouse chimeric embryos", Proc. Natl. Acad. Sci. USA. 87: 4712–4716 (1990).

Mansour, S.L., et al., "Disruption of the proto–oncogene int–2 in mouse embryo–derived stem cells: a general strategy for targeting mutations to non–selectable genes", Nature 336: 348–352 (1988).

International Search Report No. PCT/FR 90/00185 (Jun. 14, 1990).

Doetschman, T., et al., "Targeted mutation of the Hprt gene in mouse embryonic stem cells", Proc. Natl. Acad. Sci. USA 85: 8583–8587 (1988).

Johnson, R.S., et al., "Targeting of non–expressed genes in embryonic stem cells via homologous recombination", Chemical Abstracts, 111, No. 221, 188649f (1989).

Zimmer, A., et al., "Production of chimaeric mice containing embryonic embryonic stem (ES) cells carrying a homoeobox Hox 1.1 allele mutated by homologous recombination", Nature 338: 150–153 (1989).

Thompson et al., Cell 56; 313–321 (1989).

Breier et al., EMBO 7; 1329–1336 (1988).

Frohman et al., Cell 56; 145–147 (1989).

Wrischnik et al., NAR 15; 529–542 (1987).

An et al., Molecular and Cellular Biology 2; 1628–1632 (1982).

\* cited by examiner

```
              Pst I     Sal I   Bam HI      Eco RI   Sma I
pBR322 —— CT GCA G GT CGA C GG ATC CGG GGA ATT CCC 8   9              1021
    BamH I  pro val              lys  stop stop stop
GGG GAT CCC GTC ——lac Z—— AAA TAA TAA TAA CCG GGC AGG GGG GAT CCG TCG ACC TGC AG —— pBR322
              Bam HI   Sal I    Pst I
```

FIG. 8a    FIG. 8b

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
      (A) LENGTH: 14 base pairs
      (B) TYPE: nucleic acid
      (C) STRANDEDNESS: double
      (D) TOPOLOGY: linear (ii) MOLECULE TYPE: DNA (genomic)

(xi) SEQUENCE DESCRIPTION: SEQ ID NO:1:

CCAGCATGAG CTCC          14

(2) INFORMATION FOR SEQ ID NO:2:

(i) SEQUENCE CHARACTERISTICS:
      (A) LENGTH: 5 amino acids
      (B) TYPE: amino acid
      (D) TOPOLOGY: linear (ii) MOLECULE TYPE: peptide (xi) SEQUENCE DESCRIPTION: SEQ ID NO:2:

Ile Pro Gly Asp Pro
1            5

(2) INFORMATION FOR SEQ ID NO:3:

(i) SEQUENCE CHARACTERISTICS:
      (A) LENGTH: 15 base pairs
      (B) TYPE: nucleic acid
      (C) STRANDEDNESS: double
      (D) TOPOLOGY: linear (ii) MOLECULE TYPE: DNA (genomic)

(xi) SEQUENCE DESCRIPTION: SEQ ID NO:3:

ATTCCCGGGG ATCCC         15

(2) INFORMATION FOR SEQ ID NO:4:

(i) SEQUENCE CHARACTERISTICS:
      (A) LENGTH: 12 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:4:

CCAGCATGAG CT            12

(2) INFORMATION FOR SEQ ID NO:5:

(i) SEQUENCE CHARACTERISTICS:
      (A) LENGTH: 4 amino acids
      (B) TYPE: amino acid
      (D) TOPOLOGY: linear (ii) MOLECULE TYPE: peptide (xi) SEQUENCE DESCRIPTION: SEQ ID NO:5:

```
Met Gly Asp Pro
  1

(2) INFORMATION FOR SEQ ID NO:6:

(i) SEQUENCE CHARACTERISTICS:
         (A) LENGTH: 17 base pairs
         (B) TYPE: nucleic acid
         (C) STRANDEDNESS: double
         (D) TOPOLOGY: linear (ii) MOLECULE TYPE: DNA (genomic)

(xi) SEQUENCE DESCRIPTION: SEQ ID NO:6:

CCAGCATGGG GGATCCC                                                17

(2) INFORMATION FOR SEQ ID NO:7:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:7:

GTTTCGCATG                                                        10

(2) INFORMATION FOR SEQ ID NO:8:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:8:

GTGCACCATG                                                        10

(2) INFORMATION FOR SEQ ID NO:9:

(i) SEQUENCE CHARACTERISTICS:
         (A) LENGTH: 28 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:9:

CTTGTTCAAT CATGGTGCAC GATCCTCA                                    28

(2) INFORMATION FOR SEQ ID NO:10:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:10:

CCCCGGGGGT ACCTCTAGAA TGCATTCCGC                                  30
```

(2) INFORMATION FOR SEQ ID NO:11:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

GGAATGCATT CTAGAGGTAC CCCCGGGGGG CC        32

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

AACTTCCCTC TCTGCTATTC        20

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

CAGCAGAAAC ATACAAGCTG        20

(2) INFORMATION FOR SEQ ID NO:14:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

CTGCAGGTCG ACGGATCCGG GGAATTCCC        29

(2) INFORMATION FOR SEQ ID NO:15:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

GGGGATCCCG TC        12

(2) INFORMATION FOR SEQ ID NO:16:

(i) SEQUENCE CHARACTERISTICS:
        (A) LENGTH: 18 base pairs

```
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

AAATAATAAT AACCGGGC                                              18

(2) INFORMATION FOR SEQ ID NO:17:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

AGGGGGGATC CGTCGACCTG CAG                                        23
```

PROCEDURE FOR SPECIFIC REPLACEMENT OF A COPY OF A GENE PRESENT IN THE RECIPIENT GENOME BY THE INTEGRATION OF A GENE DIFFERENT FROM THAT WHERE THE INTEGRATION IS MADE

This application is a continuation of application Ser. No. 08/301,037, filed Sep. 6, 1994 U.S. Pat. No. 6,526,313, which is a continuation of application Ser. No. 08/048,056, filed Apr. 19, 1993, now abandoned, which is a continuation of application Ser. No. 07/598,679, filed Dec. 19, 1990, now abandoned, which is the National Stage of International Application No. PCT/FR90/00185, filed Mar. 19, 1990, which is based on French priority application No. FR 89/03630, filed on Mar. 20, 1989.

The invention relates to a procedure for specific replacement of a copy of a gene present in the genome of a recipient eucaryotic organism by the integration of a gene different from the inactivated gene. Preferably, the recipient gene will be present in at least 2 copies in the transfected host cell. The recipient gene is defined as being the gene where the insertion of the different gene is made.

More particularly, the invention relates to the production of transgenic animals in which the foreign gene has been introduced in a targetted manner in order to make possible both the maintainance of the normal genetic functions of the animal and the expression of the foreign gene under the control of endogenous promoters.

By "different or foreign gene" is meant any nucleotide sequence corresponding to the totality or a part of a "foreign or different" gene from the recipient gene such as is normally found in the genome (RNA or DNA), or it also correponds to an artificially modified sequence of the normal gene or also to a fragment of this sequence.

The invention also relates to the process for the production of these transgenic animals.

In the production of transgenic animals, the conventional methods used for the introduction of heterologous DNA sequences into the germinal cell line do not make it possible to control the site of integration of the foreign gene into the genome nor the number of copies thus introduced. The integration of the foreign gene occurs at random and, usually, several copies of the gene are integrated at the same time, sometimes in the form of a head-to-tail tandem, the site of integration and the number of copies integrated varying from one transgenic animal to another.

Thus, it may happen that endogenous cellular genes, situated at the point of insertion, are thus inactivated without this being easily detectable on account of the many random insertions. If the product of these genes is important for the development of the animal, the latter will be seriously perturbed. Moreover, the random insertion of the foreign gene may occur at a site which is not suitable for the expression of the gene. In addition, the fact that there may be variation in the site and in the number of insertions from animal to animal makes the interpretation of the studies of expression extremely difficult.

A major problem encountered in the production of transgenic animals is the obtaining of the expression of the foreign gene. Generally speaking, two types of experiment have been made in mice.

The genes introduced into the germ line are:
 either "complete" genes, comprising coding sequences flanked by their own regulatory sequences;
 or composite genes, composed of the coding sequence of a gene fused to a promoter sequence of another gene, the two fragments even sometimes belonging to two different animal species.

Thus, it has been possible to confirm that the specificity of the expression of the genes in this or that tissue is determined by their regulatory sequence(s).

The choice of the suitable promoter for the expression of the foreign gene in the transgenic animal is thus of primordial importance.

Furthermore, the directed mutagenesis of mouse genes in embryonic stem cells has recently been carried out by resorting to a technique of "gene targetting"(Thomas et al., 1987; Thompson et al., 1989).

In the first case, the mouse HPRT gene was mutated by insertion and replacement and, in the second case, a mutated HPRT gene was corrected. Thompson et al. have extended their experiments to the production of chimeric mice and have observed the passage of the genetic modification in the germ cell line.

In each of the documents cited, the precise site of integration was targetted by homologous recombination between, on the one hand, exogenous sequences bearing the mutation or correction included in a vector under the control of an exogenous promoter and, on the other hand, their genomic homologue. This being so, it should be noted that the earlier authors carried out their experiments on a specific gene (HPRT), the activation of which by mutation is accompanied by a detectable phenotype. The targetted mutation described by Thomas et al. had the effect of inactivating the HPRT gene and, consequently, of causing the normally detectable phenotype associated with the HPRT to disappear. The selection gene $Neo^R$, under the control of a promoter TK, was thus incorporated into the DNA to be inserted in order to make possible the selection of the transformants. It is to be noted that the experiments described in the prior art implied a selection by means of the recipient gene (e.g. HPRT) or by means of the inserted gene (eg. $Neo^R$). The site of the insertion and/or the type of gene inserted is thus limited to genes conferring a selectable character.

Furthermore, in the prior art, the exogenous sequences on the vector thus serve both to target the integration site and.to introduce the modification. Subsequent to homologous recombination, the modified gene is always found in its normal genetic environment.

Let it be recalled that a problem which arises in the course of the production of transgenic animals is the danger of inactivating an endogenous cell gene which is located at the point of insertion of the foreign gene.

Depending on the function of the product of the inactivated gene, such an inactivation may lead to extensive morphological or physiological disorders in the transgenic animal, or may even prevent its survival.

On the other hand, the inactivation of a gene might be considered to be advantageous if the gene in question codes for a receptor of a virus or other infectious agent.

The inventors have studied the possibility of avoiding the disadvantages described above and associated, in some cases, with the possible inactivation of one or several endogenous cell genes with an important function in the course of the production of transgenic animals.

The object of the invention is a process for specific replacement, in particular by targetting of a DNA, called insertion DNA, constituted by a part of a gene capable of being made functional, or the function of which may be made more effective, when it is recombined with a complementing DNA in order thus to supply a complete recombinant gene in the genome of a eucaryotic cell, characterized in that:

the site of insertion is located in a selected gene, called the recipient gene, containing the complementing DNA and in that eucaryotic cells are transfected with a vector containing an insert itself comprising the insertion DNA and two so-called "flanking" sequences on either side of the DNA of insertion, respectively homoloqous to two genomic sequences which are adjacent to the desired insertion site in the recipient gene, the insert ion DNA being heterologous with respect to the recipient gene, and the flanking sequences being selected from those which constitute the above-mentioned complementing DNA and which allow, as a result of homologous recombination with corresponding sequences in the recipient gene, the reconstitution of a complete recombinant gene in the genome of the eucaryotic cell.

The invention also relates to a procedure for the production of transgenic animals, characterized in that E.S. cells are transfected under the conditions described above and selected for the homologous recombination event, namely the correct integration of the foreign gene, the transfected cells are injected into embryos at a stage at which they are capable of integrating the transfected cells (for example at the blastocyte stage), the latter are then reimplanted in a surrogate mother and the chimeric individuals obtained at the term of pregnancy are then mated. If the E.S. cells have colonized the germ line of the chimeric animal, transgenic animals heterozygous for the replaced gene will be obtained by mating (F1) in the progeny.

It is also possible to insert the gene, borne by the vector of the invention, into the egg shortly after (i.e. less than 24 hours) fertilization. In this manner, the insertion is effected while the egg is in the unicellular state.

The invention also relates to a plasmid capable of effecting the targetted insertion of a recombinant gene, called inserted gene, in the genome of a eucaryotic cell, characterized in that it contains an insert itself comprising the insertion gene and two so-called "flanking" sequences on either side of the insertion gene respectively homologous to the two genomic sequences which are adjacent to the desired insertion site in the recipient gene.

The invention also relates to transgenic animals in which at least one endogenous gene has been inactivated by the insertion of a gene which is different from the inactivated gene, the inserted gene being inserted in a position which makes possible the expression of this gene under the control of the regulatory sequences of the inactivated endogenous gene.

Hence, as a consequence of the phenomenon of homologous recombination, the process of the invention makes it possible to insert in a targetted manner foreign genes, in particular coding sequences lacking the promoter which is normally associated with them, into the genome of a eucaryotic organism at a site which allows their expression under the control of the endogenous promoter of the gene into which the insertion is made, and consequently, enables the targetted endogenous gene to be inactivated.

According to a preferred embodiment of the invention, the targetted recipient gene is a gene which is present in the genome in at least two copies. The utilization of the technique of electro-poration (Ref. 11) ensures the introduction of one copy only of the foreign gene.

According to this variant of the invention, the targetted insertion of the gene of interest (i.e. the so-called insertion gene) has the effect of inactivating only that copy of the cellular endogenous gene at which the insertion is made and of leaving intact and functional the other copy or copies of this gene.

In this manner, the genetic functioning of the transgenic animal is not or is only slightly perturbed by the introduction of the foreign gene, even if the insertion inactivates a single copy of a recipient gene essential for the development of the animal. Thus either its development would be not effected by the insertion of the foreign gene, or the minor perturbations possible in the case of the inactivation of a critical gene would probably not be lethal for the animal. The effects of the insertion of the foreign gene in the homozygous state could be of any kind and would be observed in the 2nd generation (F2) after cross breedings of heterozygous individuals (F1) among themselves.

If, on the contrary, the inactivation of all of the copies of a gene is desired, for example, in the case in which the gene codes for a receptor of an infectious agent, multiple copies of the foreign gene are introduced. The control of the quantity introduced may be ensured by having resort to known methods.

The targetted insertion of the foreign gene thus makes possible its introduction at a site at which its expression is under the control of the regulatory sequences of the endogenous gene where the insertion is made.

The process of the invention thus makes it possible to insert the foreign gene behind an endogenous promoter which has the desired functions (for example, specificity of expression in this or that tissue), and to do so, if necessary, without inactivating the other copies of the recipient gene.

According to a particularly preferred embodiment of the invention, the insertion DNA contains between the two flanking sequences, firstly a DNA sequence designed to be recombined with the complementing DNA in the recipient gene in order to provide a recombinant gene and, secondly, a sequence coding for a selective agent making possible the selection of the transformants and a promoter allowing the expression of the selective agent, the recipient gene and the recombinant gene coding for expression products which do not confer a selectable phonotype.

In this manner, the selection of the transformants is entirely independent of the nature of the recipient gene and of the inserted gene, in contrast to the procedures described hitherto in which the inserted gene or the recipient gene had, of necessity, to code for a product of expression making possible the selection of the transformants. The system developed by the inventors allows total flexibility with respect to the nature of the recipient gene and the inserted gene or the gene formed by homologous recombination. In a surprising manner, the inventors have observed that the insertion of sequences of considerable size (for example about 7.5 kb) does not effect the frequency of homologous recombination.

The effect that the insertion of the DNA sequence may have according to this aspect of the invention includes, for example, depending on the type of sequence inserted, the replacement of a coding sequence, the replacement of a regulatory sequence, the inactivation or reactivation of a gene by mutation or the improvement of the level of expression of a gene. It is possible, according to the invention, to replace a coding phase or a part of a coding phase by a heterologous sequence which commences at the initiation codon of the replaced gene in order that the expression of the inserted gene entirely replaces the expression of the replaced gene. This avoids the formation of fusion proteins which might be undesirable in a transgenic animal.

According to this embodiment of the invention, the inserted DNA may contain between the flanking sequences a heterologous coding sequence lacking a promoter, the coding sequence being other than a gene coding for a selection agent. The insertion DNA may contain in addition, downstream from the coding sequence and still between the flanking sequences, a gene coding for a selection agent, associated with a promoter making possible its expression in the target cell.

In this manner, the heterologous coding sequence may be inserted behind an endogenous promoter which has the desired properties, for example a certain specificity of expression, or range of transcription etc., the selectibility of the transformed cells being entirely independent of the expression of the heterologous coding sequence. This type of construction makes it possible, for example, to select the transformants even though the gene replaced by the heterologous coding sequence is not normally expressed in the target cells. This is particularly important in the production of transgenic animals from embryonic stem cells since a considerable proportion of the genes remain inactive until a more advanced stage of development of the animal. The Hox-3.1 gene is an example of this type of gene. Furthermore, if the coding sequence codes for an easily detectable protein, for example the β-Gal, the development of the transcription pattern of the replaced endogenous gene may be monitored. The vector pGN is an example of this type of construction.

In accordance with another embodiment of the invention, the inserted DNA may contain a foreign regulatory sequence. The insertion site and, consequently, the flanking sequences are selected as a function of the desired purpose, namely either the insertion of the foreign regulatory sequence in order to give a "double promoter" effect with the endogenous regulatory sequence, or the replacement of an endogenous promoter by the foreign promoter. The coding sequence which is situated under the control of the regulatory sequence may be endogenous.

Another possibility would be the targetted insertion of a foreign DNA which contains both a regulatory sequence and a coding sequence. It is possible that the regulatory sequence is that which is naturally associated with the coding sequence.

The procedure of the invention makes use of a vector containing two "flanking" sequences, one on either side of the foreign gene. These flanking sequence have at least 150 base pairs and are preferably shorter than the length of the recipient gene. It is essential that the two flanking sequences be homologous with the two genomic sequences which are adjacent to the desired insertion site. The flanking sequence of the vector which is situated upstream from the foreign gene to be introduced is normally homologous to the genomic sequence which is situated on the 5' side of the insertion site. Similarly, the flanking sequence of the vector which is situated downstream from the foreign gene is normally homologous to the genomic sequence which is situated on the 3' side of the insertion site.

It is possible to introduce "intercalating" sequences between one or other of the flanking sequences and the foreign gene, for example sequences making possible the selection of the transformants, markers, sequences making possible the cloning of the vector, etc.

The position of these intercalating sequences with respect to the foreign gene must, however, be selected so as not to prevent the expression of the foreign gene, in particular of the foreign coding DNA sequence under the control of the endogenous promoter or, inversely, the endogenous DNA coding sequence under the control of foreign regulatory elements supplied by the inserted sequence.

In spite of the presence of the flanking sequences, which promote homologous recombination, it is possible that a certain number of integrations occur at random. In order to verify that the targetted insertion has indeed occurred at the targetted site and not at another site, the technique of the "Polymerase Chain Reaction" (P.C.R.) (see Ref. 10) is used in order to amplify the DNA sequence of the locus at which the insertion should be made. In this manner, only the clones transformed following homologous recombination are selected.

The flanking sequences of the vector are quite obviously selected as a function of the desired insertion site so that the homologous recombination may take place. Where appropriate, the flanking sequences may contain replica sequences of the endogenous promoter and/or modifications to the sequences which precede the initiation codon in order to improve the level of translation (sequences upstream) and replica sequences of the termination sequences, in particular poly-adenylation sites (sequences downstream).

The insertion gene may be any gene of interest. Mention should be made, as non-limiting examples, of the lac.Z gene (as in the model described below), the genes coding for interleukin or interferon, the gene for the retinoic acid or 3-beta adrenergic or H.I.V. receptor, for example, and genes known to be associated with certain diseases, for example myopathy, etc.

In accordance with a preferred variant of the invention, the eucaryotic cells are embryonic stem cells (see Ref. 14 and 15).

In fact, a mutated E.S. cell may be injected into an immature embryo which, after reimplantation, will be born in a chimeric form. If the germ line is colonized by the mutated cell, the chimeric animal will transmit the mutation to its progeny. Subsequently, it will be possible to observe the effects of this mutation in the homozygous state in some individuals, on their development, their behaviour, their metabolism, their pathology, etc.

FIG. 1 shows the plasmid pGN.

FIGS. 2a and b show the molecules pGMA and pGMD, respectively, constructed from the plasmid pGN with respect to the Hox-3.1 gene. These plasmids are plasmids of mutagenesis. The two parts of the coding phase of the Hox-3.1 gene are represented on chromosome 15 by the black box "homeo". The corresponding sequences of Hox-3.1 were cloned in the plasmid pGN. (A: polyadenylation signal; Enh/Pro: enhancer-promoter). 07 and 08 illustrate the two oligonuclueotides used in the PCR.

FIG. 6 contains the following nucleotide sequences: SEQ ID NO: 14 CTGCAGGTCGACGGATCC-GiGGGAATTCCC SEQ ID NO: 15 GGGGATCCCGTC SEQ ID NO: 16 AAATAATAATAACCGGGC SEQ ID NO: 17 AGGGGGGATCCGTCGACCTGCAG.

FIGS. 8(a) and (b) shows Southern analyses of individual positive clones (L5 and F2) and E.S. cells (C.C.E.).

Figure 8C:
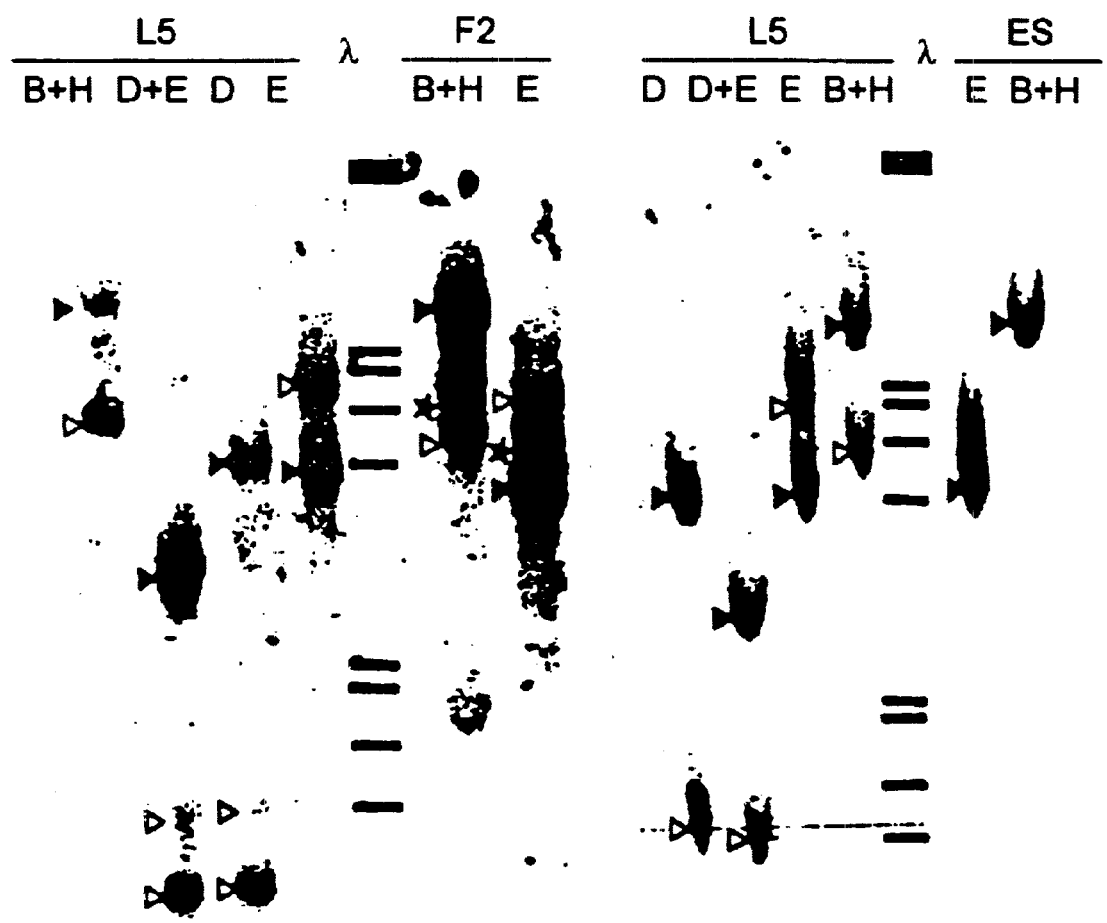

FIG. 8C depicts a restriction map of E.S. cells containing the mutated Hox-3.1 gene ("rec") in comparison with that containing the wild-type locus ("wt").

Figure 9A:
Figure 9B:
Figure 9C:

FIGS. 9A, 9B, and 9C depict chimeric embros at 9.5 and 10.5 days p.c.

The procedure of the invention is of very wide industrial application and may vary according to the nature of the foreign gene introduced.

The genetics of mammals will be able to make considerable progress as a result of the recent possibility of mutagenizing specifically any gene, thus making it possible to better define its role. By means of this technology which involves homologous recombinations and E.S. cells, valuable information will be provided concerning oncogenes, growth factors, transcription factors, etc. genes which concern very topical subjects in fundamental research or applied research. An important prospect for medical research is the possibility of reproducing a human disease whose genetic analysis is known (certain human diseases with pathology, such as Duchesne myopathy) in order to study its mechanisms better and to discover a treatment.

By applying the process of the invention, a gene known to be responsible for a certain disease is inserted in a targetted manner into the genome of a E.S. cell. The transgenic animal which is subsequently produced provides a useful model of this disease.

If necessary, and as described above, the normal genetic functions may be approximately maintained, in spite of the insertion of the foreign gene.

Another application of the process of the invention consists of inserting an insertion gene which is easily detectable e.g. the lac.Z gene and which can thus play the role of cell marker. In this manner, studies of lineage e.g. in animals entered in competitions are facilitated, and the pedigree may be monitered.

The insertion of the lac.Z gene as insertion gene also makes possible studies of the promoter. Owing to the possibility of detecting the β-galactosidase activity, the activity and specificity of various endogenous promoters may be studied by targetting different sites in the same or different types of cells. It will be possible to carry out the same studies on a whole organism, during development, or in the adult state by using the techniques of chimeric or transgenic animals.

The inventors have made the surprising observation that the frequency of homologous recombination is not effected by the insertion of fragments of large size, for example the Lac.Z. This observation suggested to the inventors that the technique of homologous recombination would be well adapted to the insertion of other heterologous genes which are of large size.

Owing to the possibility of being able to modify the genome of an animal, the process of the invention may also be used as "gene therapy". The most obvious uses would consist of inactivating the genes of receptors for infectious (viruses or bacteria) or toxic agents. If such mutagenesis were to prove lethal, it would be necessary to reestablish the lost function without reestablishing the sensitivity to the noxious agents. A modified gene coding for such a receptor could be reintroduced into the mutated cell provided that the modification could be brought about by homologous recombination. This modification of the genetic inheritance would confer on the animal an immunity against the disease under consideration.

This protocol may also be implemented in the context of auto-transplantation. Diseased or healthy cells taken from a patient could be treated and immunized, then reimplanted into the same individual.

The technique of the invention also lends itself to studies of the activity of pharmaceutical products presumed to have an activity towards the products of expression of a pathological gene associated with a disease. In this case, the inserted gene is constituted by the pathological gene and the pharmaceutical product is administered to the transgenic animal for the purpose of evaluating its activity on the disease.

The invention will be illustrated by making reference to the plasmid pGN and its use in the targetted insertion of a foreign gene (lac.Z, coding for the enzyme β-galactosidase of *E. coli*) into the genome of a E.S. cell of mice. The lac.Z gene was selected on account of the fact that its expression may be easily detected and is simply used for purposes of illustration.

The coding phase of the β-galactosidase enzyme of *E. coli* (lac.Z; 1-3057), fused with a genomic sequence (7292-3) of the mouse gene Hox. 3-1 (Ref. 1), starts with the initiation codon for this gene. In fact, the sequence which precedes the initiation codon of Hox-3.1 is identical with the consensus sequence observed in vertebrates (ref. 2), thus making possible an improved level of translation of β-galactosidase in the cells of vertebrates. The lac. Z gene is followed by a polyadenylation signal of, for example the SV 40 virus, like most of the eucaryotic genes, in order to stabilize the messenger RNAs.

The activity of the β-galactosidase of *E. coli*, which is functional in the eucaryotic cells, may be detected in different ways. Cells expressing the lac.Z gene take on a blue colour, after fixation in the presence of X-Gal, which is a substrate for β-galactosidase (Ref. 3). A new substrate, the FDG (fluoroscein di-β-galactopyranoside) makes it possible to detect and determine the β-gal. activity while keeping the cells alive (Ref 4). The cells expressing lac.Z accumulate a fluorescent product and can be isolated with the aid of a cell sorter or FACS (fluorescence-activated cell sorter).

The transcription unit of the gene for resistance to neomycin is derived, in large part, from the plasmid pRSV neo (Ref. 5). The LTR (long terminal repeat) of the Rous sarcoma virus provides very powerful promoter and enhancer sequences in many eucaryotic cells (Ref. 6). From the bacterial transposon Tn5 are derived an active promoter in *E. coli* and the coding phase of the enzyme phosphotransferase (Ref. 7), which is followed by the polyadenylation signal of the SV40 virus. The same gene under the double control of the RSV and Tn5 promoters can confer resistance to neomycin or kanamycin on bacteria and resistance to G418 on eucaryotic cells.

As a result of the effect of a simple point mutation, the B unit of the enhancer sequences of the PyEC F9.1 strain of the polyoma virus became much more active in different types of cells, and in particular in embryo carcinoma (EC) cells (Ref. 8). Two copies of this enhancer Py F9.1 were inserted in tandem into the plasmid pGN, upstream from the LTR-RSV, and in the "late promoter" orientation of the regulatory region of polyoma.

In order to improve the level of translation of the phosphotransferase, the sequence preceding the initiation codon was modified during oligonucleotide mutagenesis. Thus the sequence T T C G C A U G became G C A C C A U G, corresponding much better to the consensus initiation sequence for translation in vertebrates (Ref. 2).

It was possible to evaluate the improvements introduced into the transcription unit of the gene for resistance to neomycin by transfecting embryonic stem cells (ES) of the mouse. At equal molarity of plasmid, a construction with the Py. F9.1 enhancers produced 7.5× more resistant clones to G418 than the pRSV neo and 2 to 3× more than the pMC1 Neo described by Capecchi et al (ref. 13). Again, the number of clones was increased 60×,—that is 450× compared to the pRSV neo, by modifying the initiation sequence of translation. Homologous recombination may be a quite rare event, depending on the experimental conditions used (p. ex 1/1000 for HPRT, ref. 13). A vector possessing a high efficacy of selection is thus very useful, all the more so since the conditions of electroporation mainly give rise to the integration of a single copy.

The pGN plasmid, contains, in addition, a bacterial origin of replication of the type colE1, pBR322, which makes the clonings and preparations in *E. coli* possible.

Finally, a multiple cloning site (M.C.S.), synthesized in vitro, which only contains unique sites of cleavage in pGN, was inserted upstream from lac.Z., in order to facilitate the uses of this plasmid.

Figure 1:
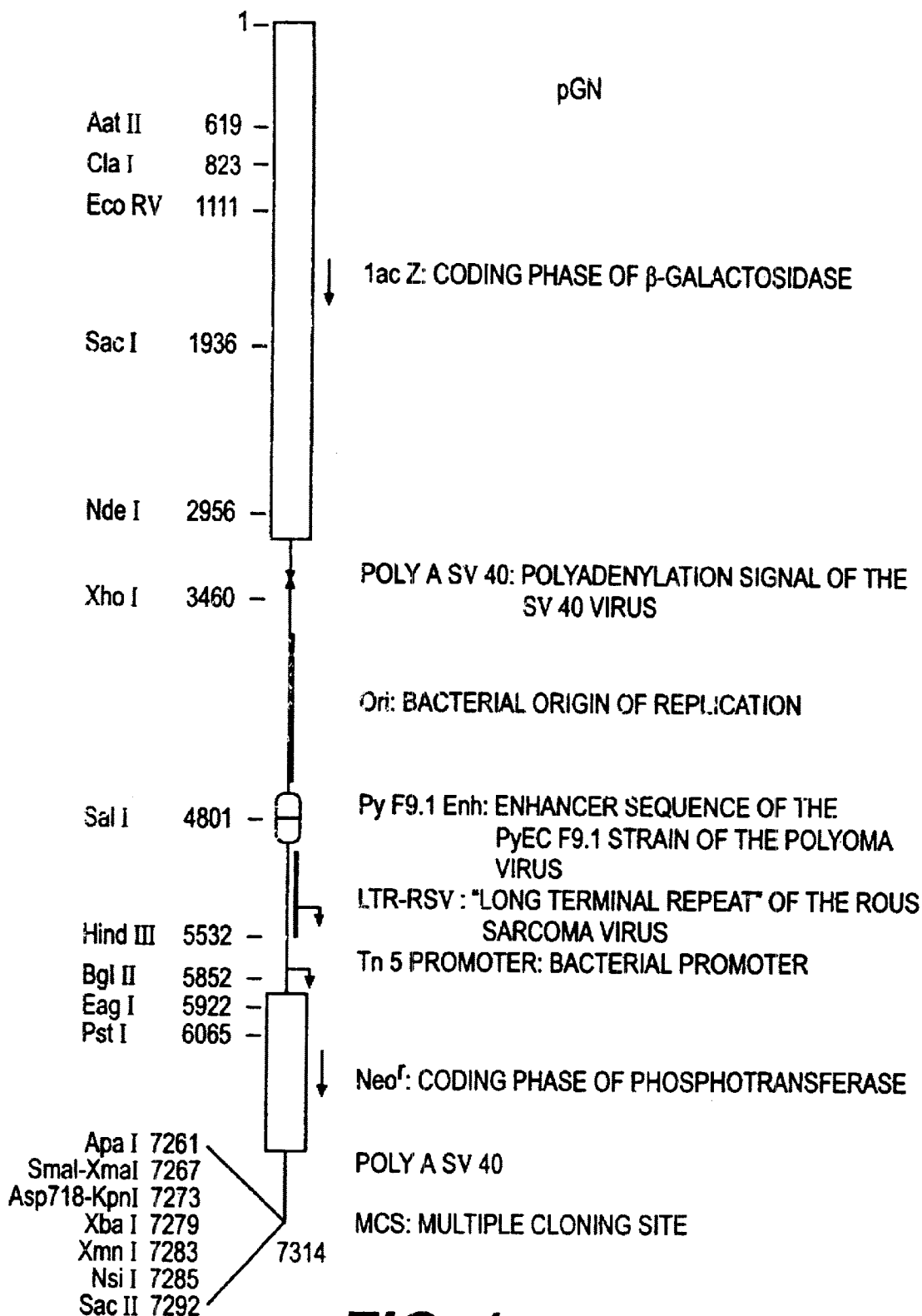
Figure 2A:
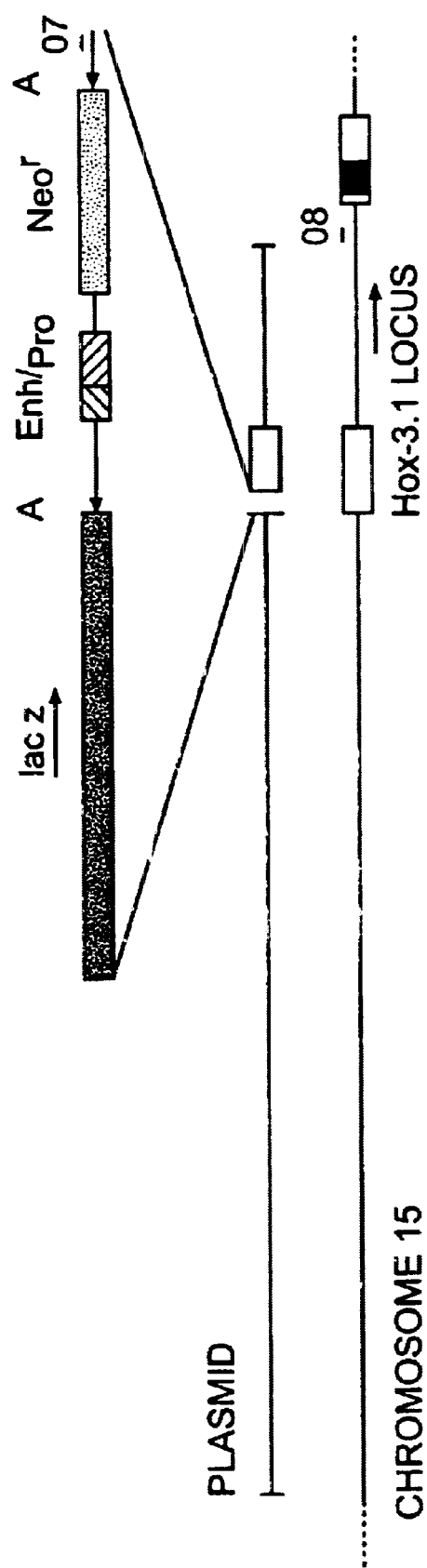
Figure 2B:
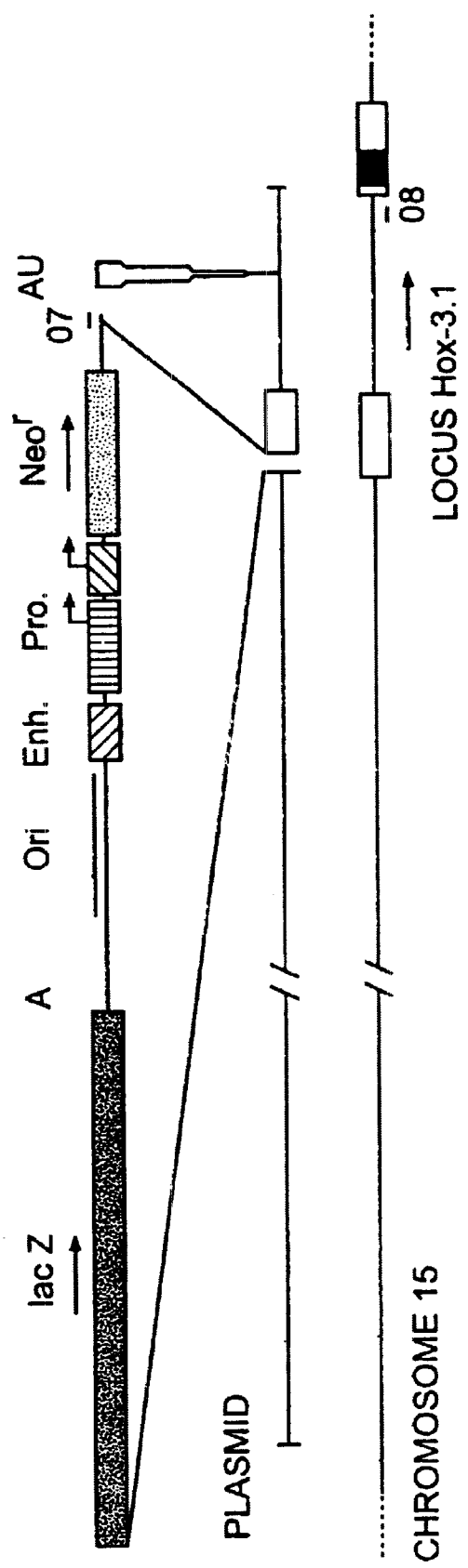
Figure 3:
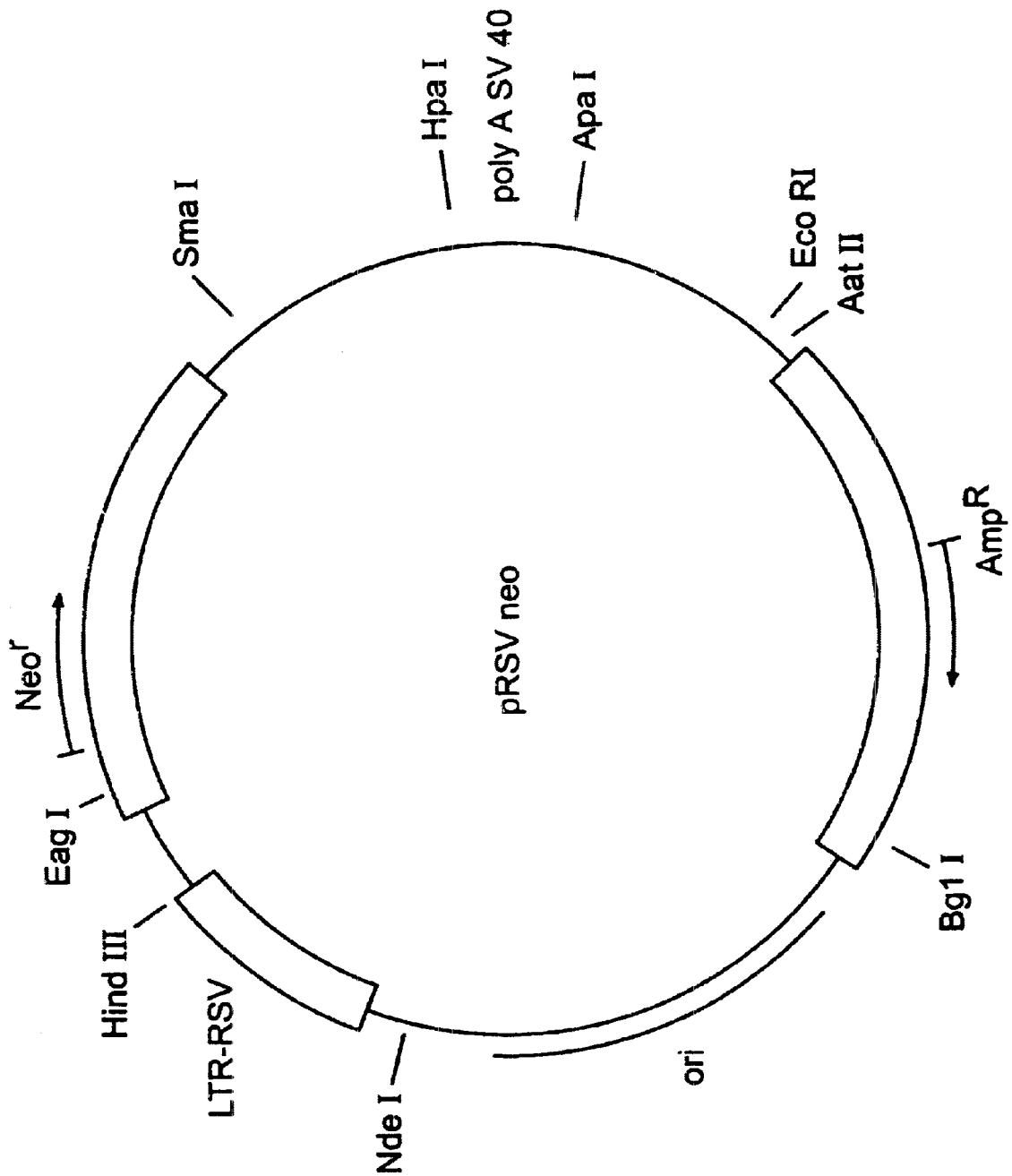
FIGS. 3 to 6 show the plasmids used in the construction of the pGN.
Figure 4:
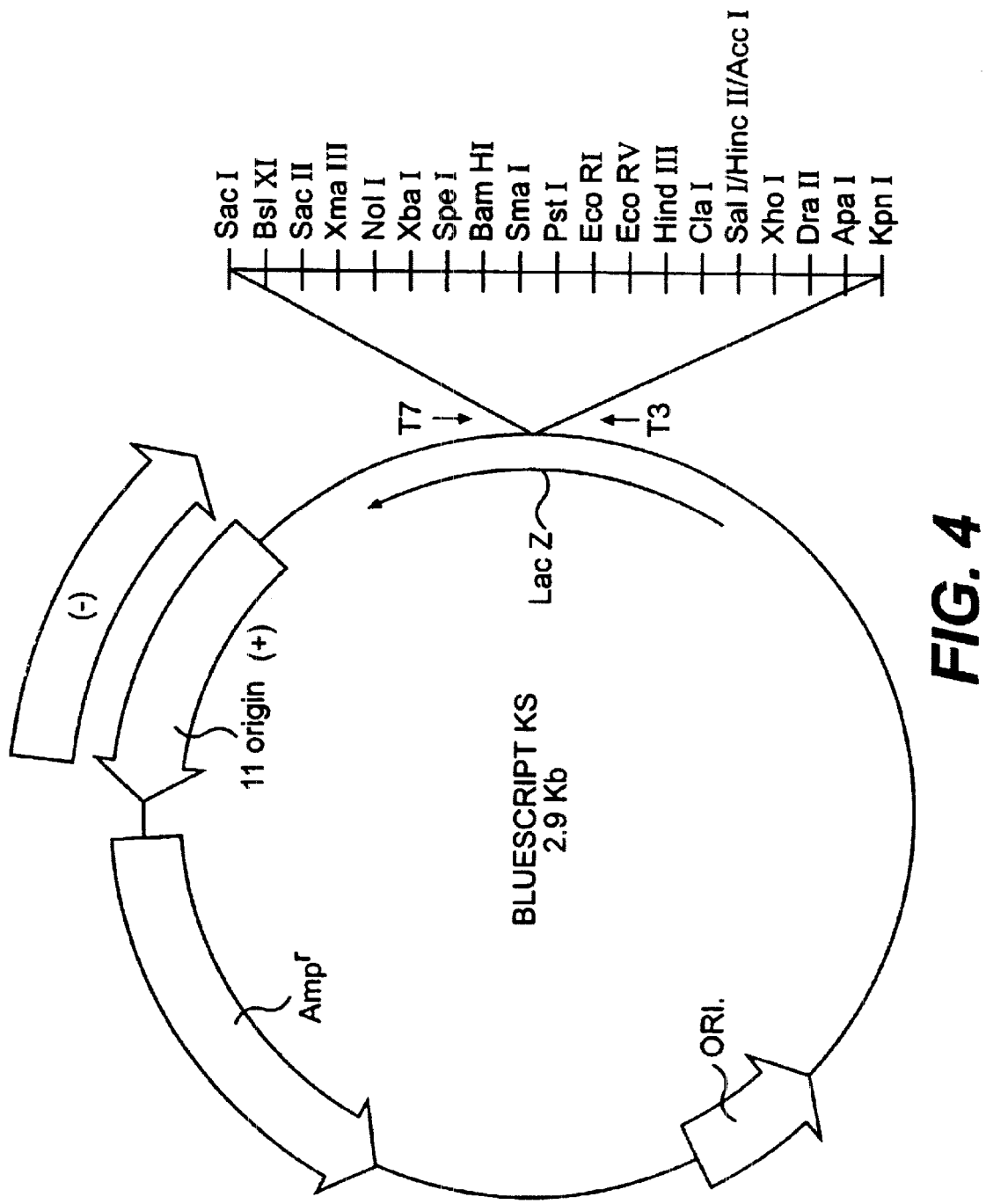
Figure 5:
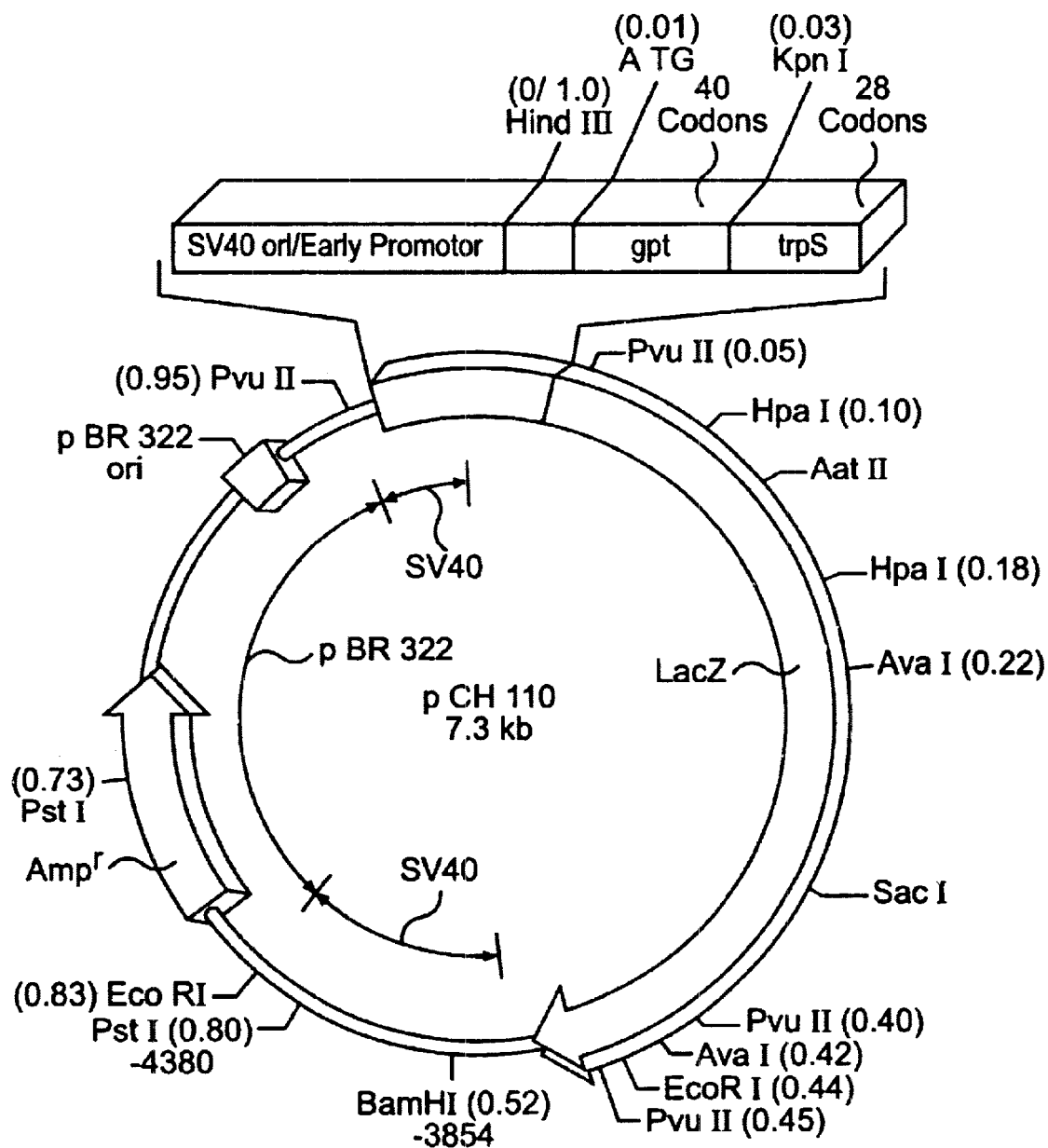
Figure 6:
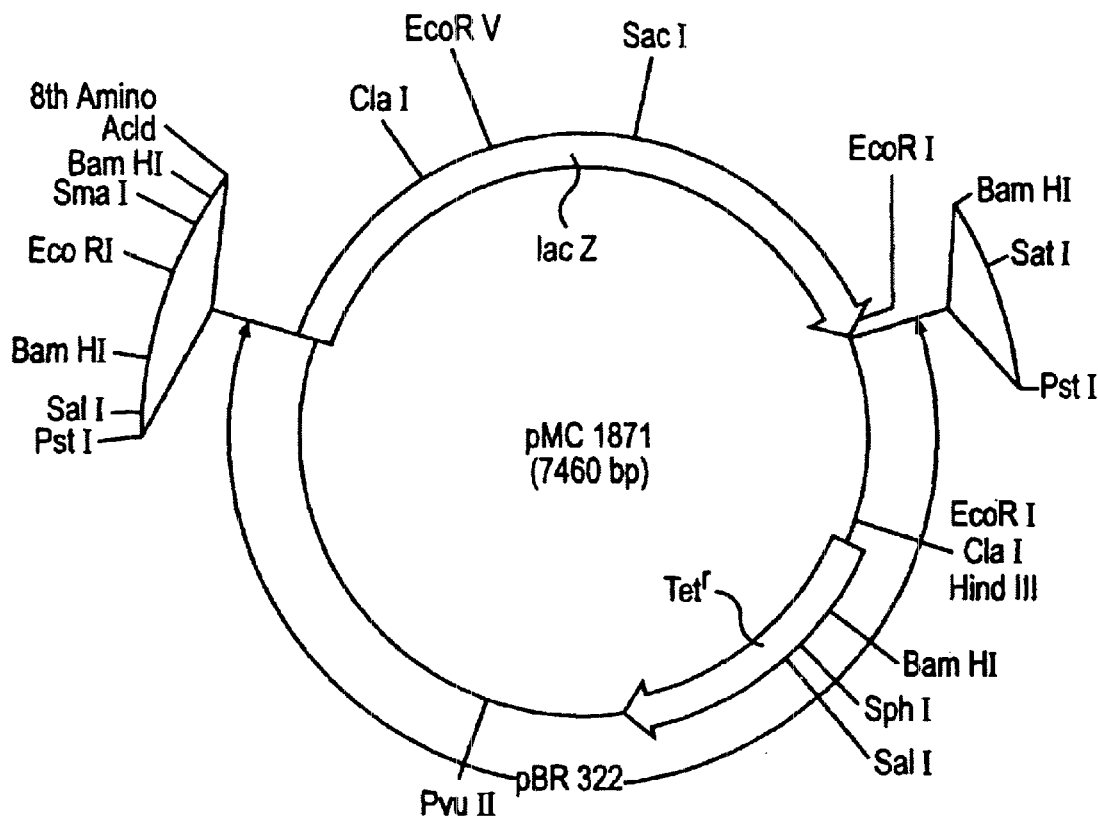

The plasmid "flanking" sequences which produce homologous recombination are added to the extremities of the pGN plasmid after linearization of the plasmid upstream from lac.Z through a site of the MCS (see FIG. 2). In this case, the flanking sequences selected are homologous with the chromosomal sequences derived from Hox-3.1 subsequently required to engage in homologous recombination.

FIG. 2 places the molecule constructed from the plasmid pGN with respect to the Hox-3.1 gene. In this case, recombination between the plasmid and chromosomal sequences of Hox-3.1 would result in an insertion at the start of the coding phase of this gene, hence in its total inactivation.

The pGN plasmid brings together several advantages for this methodology which is applicable to any gene. Since the event of homologous recombination may be quite rare (of the order of 1 for 1000 non-homologous integrations), it is necessary to be able to analyse a large number of clones whose resistance to G418 is sufficiently high as to be expressed in any part of the genome. The modifications introduced into the transcription unit of the phosphotransferase completely solve these problems. The method of mutagenesis by homologous recombination corresponds to inactivating a gene by an insertion or a substitution, but the plasmid pGN offers the additional advantage of being able to substitute the expression of β-galactosidase for that of the mutated gene. Finally, the MCS facilitates the clonings of genomic fragments.

EXAMPLES

I—Construction of the Plasmid pGN

The intermediate plasmids are numbered according to their step.

1° Step:
Insertion of a Xho I Site Into the Bgl I Site of pRSV Neo
Insertion of a Xho I linker into the Bgl I site of pRSV neo, filled in by means of the Klenow fragment of the DNA polymerase of *E.coli*.

2° Step:
Insertion of a Cla I Site Into the Nde I Site of the Plasmid p1
Insertion of a Cla I linker into the Nde I site of p1, filled in by means of the Klenow polymerase.

3° Step:
Insertion of the Enhancer Py F9.1 Into the Cla I Site of the Plasmid p2
Insertion of the enhancer Py F9.1 Pvu II-Pvu II isolated through a unique site, Acc I, into the Cla I site of p2. Selection of a clone containing two enhancers oriented in the "late promoter" sense.

4° Step:
Sma I-Hpa I Deletion From the Plasmid p3
The two enzymes give extremities with "blunt ends" which may be ligated directly. This deletion removes the intron of the t antigen of SV 40, which is not very useful and appreciably uses the size of the transcription unit of the phosphotransferase.

5° Step:
Insertion of a Xho I Site Into the Bam HI Site of pCH110
Insertion of a Xho I linker into the Bam HI site of the plasmid pCH 110 (Pharmacia), filled in by the Klenow polymerase.

6° Step:
Insertion of the 3' lac.Z-polyA SV 40 Into the Plasmid P4
The 3' part of the coding phase of β-galactosidase, followed by the polyadenylation signal of the SV 40 virus is isolated from the plasmid p5 through the sites Xho I-Aat II and cloned in the plasmid p4 through the same sites.

7° Step:
Insertion of the 5' lac.Z Into the Vector KS–
The 5' part of the coding phase of β-galactosidase is isolated from the plasmid pMC 1871 (Pharmacia) through the sites Pst I-Sac I and cloned in the vector KS– (Stratagene) through the same sites.

8° Step:
Fusion of a Hox-3.1 Genomic Sequence With the 5' lac.Z
A genomic sequence of the gene Hox-3.1, cloned in the vector KS–, is purified by successive digestions by the Sac I enzyme, then by the Mung bean nuclease and finally by the enzyme Apa I. This insert is fused with the 5' part of the coding phase of β-galactosidase by cloning in the plasmid p7 digested by means of Apa I-Sma I. The protein thus fused contains the initiation codon for the translation of the Hox-3.1 gene followed by the coding phase for β-galactosidase (subsequently verified by sequencing).

The chart below contains the following nucleotide and amino acid sequences also listed on the Sequence Listing at the end of the specification. SEQ ID NO: 1 CCAGCATGAGCTCC SEQ ID NO: 2 Ile Po Gly Asp Pro SEQ ID NO: 3 ATTCCCGGGGATCCC SEQ ID NO: 4 CCAGCATGAGCT SEQ ID NO. 5 Met Gly Asp Pro SEQ ID NO: 6 CCAGCATGGGGGATCCC.

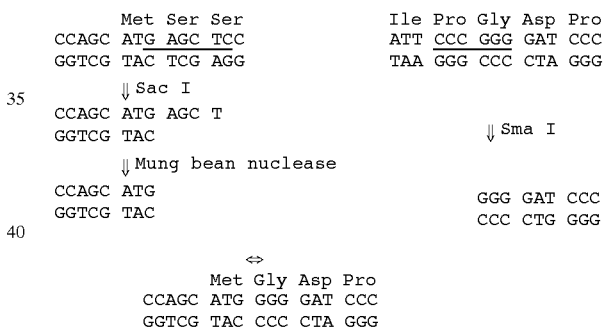

9° Step:
Insertion of Hox-3.1–5' lac.Z Into the Plasmid p6
The fusion Hox-3.1–5' lac.Z is isolated from the plasmid p8 through the sites Apa I-Sac I and cloned in the plasmid p6 through the same sites. This cloning has the effect of reconstituting the coding phase of β-galactosidase in its entirety.

10° Step:
Insertion of the Neo$^R$ Gene Into the Vector KS+
The gene for resistance to neomycin (bacterial promoter and coding phase of the phosphotransferase) is isolated from the pRSV neo through the Hind III-Eco RI sites and cloned in the vector KS+ (Stratagene).

11° Step:
Mutagenesis of the Initiation Sequence of Neo in p10
The initiation sequence of the translation of the phosphotransferase is modified in order to be identical with the consensus sequence observed in the vertebrates and thus makes possible a higher level of initiation of the translation, hence enhanced resistance to G418 in the case of mammalian cells. The modification also creates a Apa LI site which enables the effectiveness of the mutagenesis to be controlled.

The chart below contains the following nucleotide sequences. SEQ ID NO: 7 GTITCGCATG SEQ ID NO: 8 GTGCACCATG;

An oligonucleotide SEQ ID NO: 9 (CTTGTTCAATCATGGTGCACGATCCTCA) comprising a region of mismatching with the sequence of the pSRV neo (underlined) is synthesized (Gene Assembler, Pharmacia), then phosphorylated by the polynucleotide kinase of the bacteriophage T4. A single-stranded matrix of the plasmid p10 is prepared as a result of the f1 origin of the plasmid KS+ and hybridized with the oligonucleotide of mutagenesis. The second strand is synthesized and repaired by the Klenow polymerase and the DNA ligase of the bacteriophage T4. After transformation of bacteria, the mutated clones are screened with the aid of the oligonucleotide labelled with $^{32}P$. The mutagenesis was verified by digesting with Apa LI as well as by sequencing.

12° Step:

Replacement of the Initiation Sequence in the Plasmid p9

A fragment containing the modified initiation sequence for the translation of the gene for resistance to neomycin is isolated from the plasmid p11 by means of the enzymes Hind III-Eag I and cloned in the plasmid p9 through the same sites.

13° Step:

Insertion of the Multiple Cloning Site Into the Plasmid p12

Two complementary oligonucleotides are synthesized (Gene Assembler, Pharmacia), then phosphorylated. After matching, the MCS is cloned into the Apa I-Sac II sites of the plasmid p12 through its cohesive ends.

The chart below contains the following nucleotide sequences. SEQ ID NO: 10 CCCCGGGGGTACCTCTA-GAATGCATTCCGC SEQ ID NO: 11 GGAATGCAT-TCTAGAGGTACCCGGGGGGCC.

pGN in the Nsi I-Sac II and the Apa I-Nsi I sites, respectively. The sequence of the cDNA of Hox-3.1 c21 has been published (ref. 1).

The plasmid of mutagenesis is linearised by digestion with Nsi I before electroporation of the E.S. cells. Its extremities are formed of two genomic arms cloned at the Apa I-Nsi I and the Nsi I-Sac II sites of the vector pGN.

The plasmid pGMD does not possess a polyadenylation signal after the resistance gene but, on the contrary, does possess a region rich in AU responsible for the selective degradation of mRNA, inserted into the sequence of the intron of the Hox-3.1 of the plasmid.

Another plasmid of mutagenesis, pGtA, possesses the same structure as pGMD but contains the signals for polyadenylation and termination of transcription of the SV40 and does not possess the AU sequence for the degradation of mRNA downstream from the Neo$^r$ gene. The purpose of these modifications is to reduce the level of transcripts of the Neo$^r$ in the clones derived from random integration. On the other hand, clones derived from homologous recombination events between pGMD and a Hox-3.1 locus should have inaltered growth during the selection with G418, the AT sequence for the degradation of mRNA being removed by the recombination procedure itself or spliced with the intron Hox-3.1.

In the experimental steps which follow, the protocol described by Thompson et al., 1989 was followed for the production of chimeric animals.

III—Transfection of Mouse Embryonic Cells

The method described by Thompson et al. 1989, was used in order to transfect mouse embryonic cells. The use of the technique of electroporation ensures the introduction of a single copy of the foreign gene (lac.Z) per cell. After transfection, several clones expressing β-galactosidase were isolated.

The plasmids of mutagenesis pGMD and pGMA were linearised and introduced by electroporation into E.S. cells

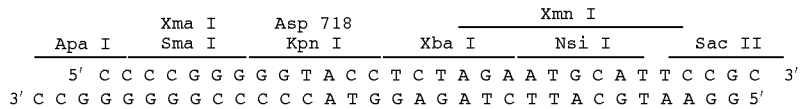

The multiple cloning site was also verified by sequencing.

II—Addition of the "Flanking" Sequences to the Extremities of the Linearised Plasmid pGN Upstream From lac.Z' Through a Site of the M.C.S.

The flanking sequences used were selected as a function of the desired insertion site (for example, Hox-3.1, see FIG. 2a and b pGMA and pGMD).

In the construction of the plasmid of mutagenesis pGMD, two arms of DNA homologous to the Hox-3.1 locus were cloned at the Apa I-Nsi I and Nsi I-Sac II sites of the vector pGN. The 5' arm starts at the Sac II site (CCGCGG) at the nucleotide 219 of the cDNA c21 of Hox-3.1. This fragment extends for 6.8 kb at the 5' up to the first BamHI site. The 3' arm starts at the Apa 1 site (GGGCCC) at the nucleotide 885 of the cDNA c21. This fragment extends for 1.5 kb at the 3' up to the first PstI site. A NsiI linker was inserted into the BamHI site of the 5' fragment and into the PstI site of the 3' fragment. The 5' and 3' arms were cloned in the vector in order to promote the insertion of one copy only into the genome (ref. 11).

The initial transfections were carried out in order to compare the efficiency of screening of the Hox-3.1 of the plasmids pGMA and pGMD (see table I).

TABLE I

Homologous recombination in the Hox-3.1 gene

| Exp. | Plasmid of muta-genes | N* of the set analysed | No. of clones forming the set | No. of positive P.C.R. results |
|---|---|---|---|---|
| I | pGMA | 3 | 600 | 0 (2) |
| II | pGMD | 5 | 250 | 3 (5) |
| III | pGMD | 84 | 2–3 | 5 (5) |

The E.S. cell line "C.C.E." (ref.16) was maintained continuously on fibroblast nurse cell layers (ref. 17). For the experiments I and II, 1.5×10$^7$ E.S. cells in 1.5 ml of HeBS were electroporated (ref. 11) at 200 V with 40 mg of linearised plasmid, then spread on four culture dishes (diameter 100 mm). For experiment III, the shock was administered under the same conditions but a quarter of the cells were spread on four plates with 24 wells. The next day, 250 μg ml$^{-1}$ G418 were added. Each transfection gave rise to about 2400 clones with pGMA and about 1000 clones with pGMD.

The mean number of clones of E.S. cells resistant to G418 in each set is indicated in table I, as well as the number of sets giving a positive result with the P.C.R. technique. A positive result means that it was possible to observe a band of 1.6 kb on an agarose gel stained with ethidium bromide (see FIG. 7). The number of sets giving a positive signal after a Southern analysis of the P.C.R. mixture and hybridization with a specific probe which did not contain the sequences of the primers is indicated in parentheses (FIG. 8).

Detection of Homologous Recombination With the P.C.R.

Figure 7:
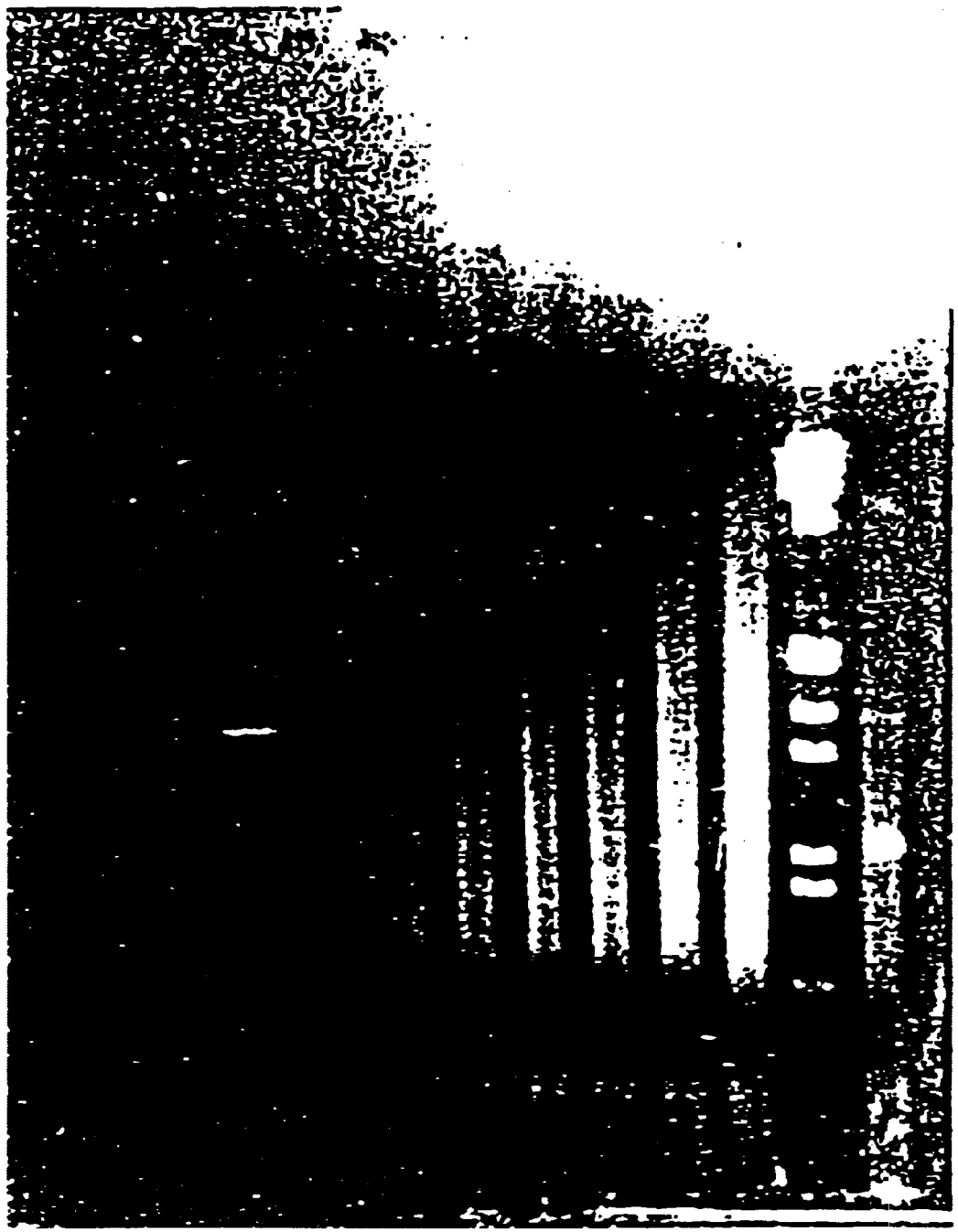
FIG. 7 illustrates the detection of homologous recombination with the Polymerase Chain Reaction (P.C.R) technique on transfected E.S. cells.
Figure 8C:
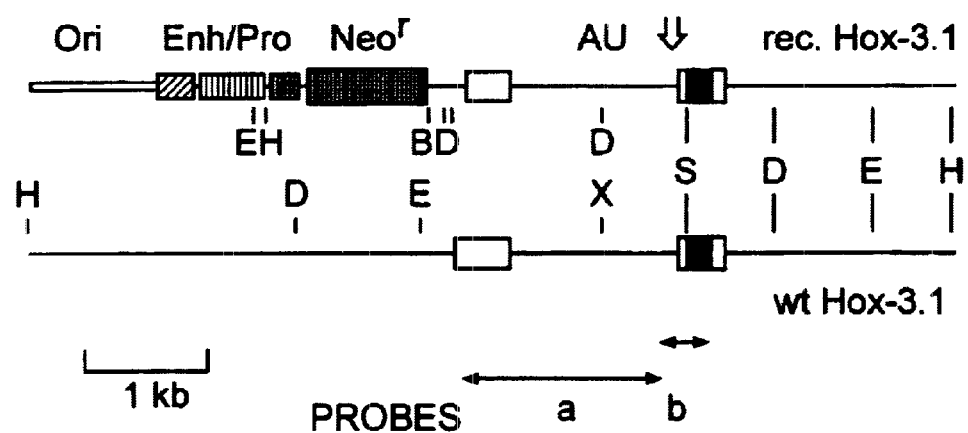

P.C.R. was carried out on 10$^5$ cells of a set of 250 clones of the transfection II (see lane D of FIG. 7). In the other lanes, four sets of the transfection III were analysed together by mixing about 4×5000 cells. The primers 07 and 08 used in the P.C.R. surround the sequence 3' Hox-3.1 of the plasmid of mutagenesis (FIG. 2). The 1.6 kb fragment covering this 3' sequence can only be amplified in the case of homologous recombination. The lanes 2, 3 and D illustrate positive results.

The DNA of the E.S. clones was prepared at the time of the replica on a filter using the method "boiling-proteinase K digestion boiling" (ref. 18). 40 cycles of amplification (40 seconds at 94° C., 1 minute at 60° C., 7 minutes at 72° C.) were performed in a reaction mixture of 100 μl, containing 67 mM Tris-HCL (pH 8.6), 16.7 mM (NH$_4$)$_2$SO$_4$, 6.7 mM MgCl$_2$, 10 mM 2-mercaptoethanol, 0.01% (wt/v) gelatin, 200 μM dATP, dTTP and dCTP, 100 μM dGTP, 100 μM 7-deaza-dGT, 600 ng of each primer (07 SEQ ID NO: 12: AACTTCCCTCTCTGCTATTC and 08 SEQ ID NO: 13: CAGCAGAAACATACAAGCTG) and 3U Taq polymerase (Perkin Elmer Cetus), covered with 100 μl of paraffin.

Half of the reaction mixture was applied to a 0.7% agarose gel stained with ethidium bromide. The size marker is a Eco RI+Hind III digest of lambda DNA.

Southern Analyses

Three independent clones of E.S. cells containing the mutated Hox-3.1 (identified by P.C.R.) were isolated from the positive sets by using pipettes. Their DNA was examined by means of Southern analysis after digestion with the restriction enzymes indicated in FIG. 8 in order to confirm the specific screening and to distinguish between the recombined and wild-type loci. Two different probes were used in the analysis of the 3' end of the Hox-3.1 loci in the mutated clones and in the non-mutated E.S. cells serving as controls (FIG. 8c). The first probe "a" was contained in the Hox-3.1 sequences of the plasmid of mutagenesis and demonstrated the number of integrations of vector and their physical linkages. One of the three recombined clones contained, in addition, a copy of the plasmid integrated at random (FIG. 8 a, clone F2). The second probe "b" which was not contained in the vector of mutagenesis distinguished between the recombined and wild-type Hox-3.1 alleles (FIG. 8b). The recombined Hox-3.1 locus showed with both probes the pattern of hybridization expected from the restriction maps of the vector of mutagenesis and the intact locus. Furthermore, the existence of two recombination domains in the 3' arm of the vector was confirmed by the presence or absence of the AT sequence in the recombined Hox-3.1 locus (for example FIG. 8, clone L5). The 5' end of the Hox-3.1 locus was also analysed for the homologous recombination event. Restriction enzymes not possessing sites in the 5' Hox-3.1 sequence of 6.8 kb of the vector of mutagenesis were used in the digestion of the DNAs of the recombined clones. These DNAs were then subjected to electrophoresis in a pulsed field in order to distinguish the fragments of high molecular weight. A Southern analysis of this gel also showed the recombined alleles correctly and the wild-type Hox-3.1 alleles by using a probe possessing a sequence upstream from the plasmid of mutagenesis.

The Southern analyses demonstrated that an allele of the Hox-3.1 gene had recombined as expected. The homologous recombination was equivalent to a double "crossing-over" between the genomic arms of the plasmid of mutagenesis and the homologous chromosomal sequences (FIG. 2).

In the recombinant clones, the lac Z gene has been placed under the control of the promoter and regulatory sequences of the Hox-3.1 upstream from the AUG codon, but the 3' maturation signals of the mRNA were derived from the SV40. In these recombined clones, the expression of lac.Z was not detectable by staining with β-Gal which is consistent with the absence of transcription of Hox-3.1 in E.S. cells determined by RNase protection analysis. The activity of β-Gal could be induced in some cells after 3 or 4 days of culture in the presence of 5.10$^{-7}$M retinoic acid, known conditions for inducing the transcription of Hox-3.1 (ref. 19).

By using the vector of mutagenesis pGMA, which possesses a total homology of 8.3 kb DNA with the Hox-3.1 locus, a fragment of 120 bp was replaced by an insertion of 7.2 kb. The frequency of this targetted replacement (1/900) is comparable to that obtained recently (1/1000) with HPRT (ref. 13) or with En-2 (1/260) (ref. 20), the heterologous fragment inserted being, however, much smaller (1.1 and 1.5 kb, respectively) in these latter cases. Surprisingly, it was observed that a very high frequency of homologous recombination (1/40) could be obtained with the vector pGMD. The removal of the 3' maturation signals for mRNA and the addition of the sequence for the degradation of mRNA to the gene for the resistance to neomycin had the effect of reducing the total number of clones resistant to G418 by 2.4 (table I). The specific screening ratio was almost 10 times higher (900/40). Even the mechanism of homologous recombination must have been affected in the experiments with pGMD. A possible explanation of these results would be that a AT sequence of 51 bp could provide, in vivo, an open loop in the plasmid of mutagenesis owing to its lower melting temperature. If the neighbouring Hox-3.1 sequences of the pGMD can be influenced by this opening, on each side of the AT region, they could react more effectively in the single-stranded state with the Hox-3.1 chromosomal locus. The model of mitotic recombination in yeast suggests that it is initiated by such an exchange of strands, whereas the mechanism of homologous recombination remains unknown in the more complex eucaryotes.

FIG. 8 shows the results of the Southern analysis performed on positive individual clones (L5 and F2) and on E.S. cells (C.C.E.).

The probes used hybridize only with Hox-3.1 sequences included in the vector (a) or excluded from the vector of mutagenesis (b). The pattern of hybridization of the recombined Hox-3.1 locus (open triangles) is clearly distinguished from the wild-type locus (black triangles). The stars indicate the hybridization bands of a copy of the plasmid which has been integrated at random. The size marker is a Eco RI+Hind III digest of lambda DNA.

The FIG. 8(c) shows the restriction maps of the recombined (rec.) and wild-type (wt) Hox-3.1 alleles. The parts of the vector of mutagenesis and of the Hox-3.1 locus are indicated with the same symbols as those used in FIG. 2. In this case, the AT sequence has been integrated by homologous recombination. The vertical arrow indicates the 3' end of the plasmid of mutagenesis. The location of the "a" and "b" probes used in the Southern analysis is also indicated. The abbreviations used in FIG. 8 are the following: B, Bam HI; D, Dra I, E, Eco RI; H, Hind III; S, Sal I; X, Xho I.

IV—Production of Chimeric Embryos

A microinjection into blastocysts was carried out with two recombinant E.S. clones containing an intact Hox-3.1 allele and a recombined allele, these clones did not contain any other copy of the plasmid of mutagenesis. The karyotypes of the cells were normal.

Ten to fifteen mutated cells were microinjected per blastocyst. After reimplantation in surrogate mothers, the embryos were collected at 9.5, 10.5 and 12.5 days p.c. and analysed for the expression of lac.Z. The range of transcription of Hox-3.1 at these stages had been determined beforehand by in situ hybridization analysis (ref. 1). The Hox-3.1 transcripts are detectable for the first time at the stage of late gastrulation and are distributed in all of the tissues of the posterior part of the animal. Later, the distribution becomes progressively limited in space and specific with respect to tissue. At the stage of 12.5 days p.c., transcription is localized in the cervical region of the neural tube, at the level of the heart. During the course of embryogenesis, the distribution of the transcription of Hox-3.1 thus undergoes modifications. The 10.5 days p.c. stage seems to be a period of transition, transcription taking place both in the two posterior regions and in the cervical neural tube.

In chimeric embryos at 9.5 and 10.5 days p.c., the caudal part of the posterior bud exhibited intense β-Gal activity, whereas the marker was never detected in the anterior thoracic region or the head (FIG. 9a). In the posterior region, cells stained by β-Gal were observed in all of the tissues and all of the embryonic strata. Between the two buds which give rise to the limbs, stained cells were distributed in restricted zones, in the superficial ectoderm (FIG. 9b) as in the posterior regions (FIG. 9c) and, in the form of narrow lines or stripes, in the neural tube (FIG. 9b). These stripes showed an irregular and asymmetric distribution in the wall of the neural tube. The transcription of Hox-3.1 was not detected in the thin layer of cells towards the closure of the neural tube. These cells did not perhaps withstand the treatments used during the in situ hybridization. It has been observed that the cells of the neural ectoderm very early form part of different parts of the nervous system and migrate in a radial direction, following restricted lateral movements (ref. 21). These results are thus consistent with that observation.

The expression of Lac.Z has thus correctly illustrated the first part of the transcription of the homeogene Hox-3.1, i.e. in all of the tissues of the caudal regions of the embryos at 9.5 and 10.5 days p.c., and has provided novel information concerning the mode of transcription of Hox-3.1.

On the other hand, the expression of Lac.Z has not been observed in the cervical regions of the neural tube of chimeric embryos at 12.5 days, nor in the anterior region of embryos at 10.5 days; this was not the result expected from the studies of in situ hybridization. The subsequent phase of transcription of Hox-3.1 observed from day 10.5 in the very localized zones of the neural tube was not characterized by the activity of β-Gal. One possible explanation for this result would be that, whereas the expression of lac.Z is under the control of the Hox-3.1 promoter, the 3' sequences of the Hox-3.1 are absent from the reporter gene. It is possible that 3' sequences of the initiation codon AUG of the Hox-3.1 have an influence on the late expression of Hox-3.1 in the anterior domain. An effect of "gene dosage" could also explain this result. The autoactivation of several homeogenes in Drosophila has been demonstrated genetically or suggested by the formation of complexes between the DNA and the proteins of the homeobox.

If the late component of the transcription of Hox-3.1 in the neural tube is maintained by a similar mechanism, the inactivation of an allele would have a dominant effect in the cells of the neural ectoderm. Since one allele only would produce the Hox-3.1 protein, the activation signal would be diluted on the two promoters. The reduction of autoinactivation in the two loci would thus be able to bring the initiation of transcription to a complete stop. This would explain why no expression of Lac.Z was detected in the cervical region of the neural tube of embryos at 10.5 and 12.5 days.

V—Passage of the Modification Into the Germ Cell Line: Production of Transgenic Animals The effects in $F_1$ and $F_2$ of the modification introduced by the targetted insertion were observed after reproduction of the chimeras. The passage of the modification into the germ cell line was noted.

BIBLIOGRAPHY

1. Le Mouellic, H., Condamine, H. et Brulet, P. (1988). Genes & Development. 2, 125–135.
2. Cavenir, D. R. (1987). Nucleic Acids Res. 15, 1353–1361.
3. Sanes, J. R. Rubenstein, J. L. R. et Nicolas, J. F. (1986) EMBO J. 5, 3133–3142.
4. Nolan, G. P., Fiering, S., Nicolas, J. F. et Herzenberg, L. A. (1988) Proc. Natl. Acad. Sci. USA 85, 2603–2607.
5. Gorman, C., Padmanabhan, R. et Howard, B. H. (1983). Science. 221, 661–553.
6. Gormann, C. M., Merlino, G. T. Willingham, M. C. Pastan, I. et Howard, B. H. (1982) Proc. Natl. Acad. Sci. USA 79, 6777–6781.
7. Southern, P. J. et Berg, P. (1982) J. Mol. Appl. Genet 1, 327–341.
8. Herbomel, P., Bourachot, B. et Yaniv, M. (1984). Cell. 39, 653–662.
9. Robertson, E. J. (1987). Teratocarcinomas and embruonic stem cells: A practical approach. IRL Press, Oxford.
10. Kahn, A. (1988). Medecine/Sciences 4, 515–518.
11. G. Chu, Hayakawa H., Berg. P. (1987) Nucleic Acid Research 15, Nr. 3, 1311–1326.
12. Thompson, S., Clarke, A. R., Pow, A. M., Hooper, M. L., Melton, D. W., (1989) Cell, 56, 313–321.
13. Thomas, K. R., Capecchi, M. R., (1987) Cell, 51 503–512.
14. Evans, M. J., Kaufmann, M. H. (1981) Nature, 292, 154–155,
15. Robertson, E. J., (1986) Trends in Genetics, 9–13
16. Robertson, E., Bradley, A., Kuehn, M. & Evans, M. Nature 323, 445–448 (1986).
17. Robertson, E. J. in Teratocarcinomas and Embryonic Stem Cells (ed. Robertson, E. J.) 71–112 (IRL, Oxford, 1987).
18. Kim, H. S. & Smithies, O. Nucleic Acids Res. 16, 8887–8903 (1988).
19. Breier, G., Bucan, M., Francke, U., Colberg-Poley, A. M. & Gruss, P. EMBO J. 5, 2209–2215 (1986).
20. Joyner, A. L., Skarnes, W. C. & Rossant, J. Nature 338, 153–156 (1989).
21. McKay, R. D. G. Cell 58, 815–821 (1989).

What is claimed is:

1. An in vitro process for providing a recombinant DNA sequence, wherein the process comprises:
   (A) providing a mammalian cell having a recipient DNA sequence, wherein said recipient DNA sequence comprises complementing DNA comprising a first nucleotide sequence and a second nucleotide sequence downstream of said first nucleotide sequence;
   (B) transfecting said mammalian cell in vitro with a transfection DNA comprising:
      (1) a third nucleotide sequence homologous to said first nucleotide sequence;
      (2) a fourth nucleotide sequence homologous to said second nucleotide sequence; and
      (3) a DNA sequence heterologous with respect to said recipient DNA sequence, wherein said heterologous DNA sequence is between said third and said fourth nucleotide sequences and said heterologous DNA sequence comprises a first insertion DNA sequence and a second insertion DNA sequence, wherein said first insertion DNA sequence comprises a first coding sequence that encodes a first product that does not confer resistance to a selection agent involved in the selection of transformants, and said second insertion DNA sequence comprises a second coding sequence that encodes a second product that confers resistance to a selection agent involved in the selection of transformants, and a promoter allowing the expression of said second product in said mammalian cell;
   (C) selecting a transfected cell in which said heterologous DNA sequence has been inserted between said first and said second nucleotide sequences in said recipient DNA sequence by homologous recombination with said third and said fourth nucleotide sequences to thereby provide a mammalian cell containing the recombinant DNA sequence, and in addition, the second insertion DNA sequence encoding the selective agent; and
   (D) recovering said recombinant DNA sequence from said mammalian cell.

2. The in vitro process as claimed in claim 1, wherein insertion of said heterologous DNA sequence in said recipient DNA sequence is accompanied by replacement of recipient DNA sequence DNA.

3. The in vitro process as claimed in claim 1, wherein each of said third and said fourth nucleotide sequences has a length greater than 150 base pairs and shorter than the length of said recipient DNA sequence.

4. The in vitro process as claimed in claim 1, wherein said recipient DNA sequence is present in said mammalian cell in at least two copies and said heterologous DNA sequence is inserted into only one copy of said recipient DNA sequence.

5. The in vitro process as claimed in claim 1, wherein said first coding sequence encodes an interferon, an interleukin, a β-3-adrenergic receptor, a retinoic acid receptor, an HIV receptor, or lac Z.

6. The in vitro process as claimed in claim 1, wherein said first coding sequence encodes lac Z.

7. The in vitro process as claimed in claim 1, wherein said mammalian cell is a mouse embryonic stem (E. S.) cell.

8. The in vitro process as claimed in claim 1, wherein said transfection is by electroporation.

9. The in vitro process as claimed in claim 1, wherein the selective agent is neomycin.

10. The in vitro process as claimed in claim 1, wherein said second insertion DNA sequence lacks a polyadenylation sequence and is operably linked at the 3' end to a 5' region of an intron containing a sequence that causes the selective degradation of transcripts of said heterologous DNA sequence.

11. The in vitro process as claimed in claim 10, wherein the process further comprises achieving a homologous recombination frequency ratio of at least 1 homologous recombination event per 900 random insertion events.

12. The in vitro process as claimed in claim 10, wherein the process further comprises achieving a homologous recombination frequency ratio of at least 1 homologous recombination event per 40 random insertion events.

13. The in vitro process as claimed in claim 1, wherein the process further comprises achieving a homologous recombination frequency ratio of at least 1 homologous recombination event per 900 random insertion events.

14. The in vitro process as claimed in claim 1, wherein the process further comprises achieving a homologous recombination frequency ratio of at least 1 homologous recombination event per 40 random insertion events.

15. An in vitro process for providing a recombinant DNA sequence, wherein the process comprises:
  (A) providing a mammalian cell having a recipient DNA sequence, wherein said recipient DNA sequence comprises complementing DNA comprising a first nucleotide sequence and a second nucleotide sequence downstream of said first nucleotide sequence;
  (B) transfecting said mammalian cell in vitro with a transfection DNA comprising:
    (1) a third nucleotide sequence homologous to said first nucleotide sequence;
    (2) a fourth nucleotide sequence homologous to said second nucleotide sequence; and
    (3) a DNA sequence heterologous with respect to said recipient DNA sequence, wherein said heterologous DNA sequence is between said third and said fourth nucleotide sequences and said heterologous DNA sequence comprises a first insertion DNA sequence and a second insertion DNA sequence, wherein said first insertion DNA sequence comprises a first coding sequence that encodes a first product that does not confer resistance to a selection agent involved in the selection of transformants, and a regulatory sequence for regulating the expression of said first product, and said second insertion DNA sequence comprises a second coding sequence that encodes a second product that confers resistance to a selection agent involved in the selection of transformants, and a promoter allowing the expression of said second product in said mammalian cell;
  (C) selecting a transfected cell in which said heterologous DNA sequence has been inserted between said first and said second nucleotide sequences in said recipient DNA sequence by homologous recombination with said third and said fourth nucleotide sequences to thereby provide a mammalian cell containing the recombinant DNA sequence, and in addition, the second insertion DNA sequence encoding the selective agent; and
  (D) recovering said recombinant DNA sequence from said mammalian cell.

16. The in vitro process as claimed in claim 15, wherein said regulatory sequence is a promoter.

17. The in vitro process as claimed in claim 15, wherein said regulatory sequence is an enhancer.

18. The in vitro process as claimed in claim 15, wherein insertion of said heterologous DNA sequence in said recipient DNA sequence is accompanied by replacement of recipient DNA sequence DNA.

19. The in vitro process as claimed in claim 15, wherein each of said third and said fourth nucleotide sequences has a length greater than 150 base pairs and shorter than the length of said recipient DNA sequence.

20. The in vitro process as claimed in claim 15, wherein said recipient DNA sequence is present in said mammalian cell in at least two copies and said heterologous DNA sequence is inserted into only one copy of said recipient DNA sequence.

21. The in vitro process as claimed in claim 15, wherein said first coding sequence encodes an interferon, an interleukin, a β-3-adrenergic receptor, a retinoic acid receptor, an HIV receptor, or lac Z.

22. The in vitro process as claimed in claim 15, wherein said first coding sequence encodes lac Z.

23. The in vitro process as claimed in claim 15, wherein said mammalian cell is a mouse embryonic stem (E. S.) cell.

24. The in vitro process as claimed in claim 15, wherein said transfection is by electroporation.

25. The in vitro process as claimed in claim 15, wherein the selective agent is neomycin.

26. The in vitro process as claimed in claim 15, wherein said second insertion DNA sequence lacks a polyadenylation sequence and is operably linked at the 3' end to a 5' region of an intron containing a sequence that causes the selective degradation of transcripts of said heterologous DNA sequence.

27. The in vitro process as claimed in claim 26, wherein the process further comprises achieving a homologous recombination frequency ratio of at least 1 homologous recombination event per 900 random insertion events.

28. The in vitro process as claimed in claim 26, wherein the process further comprises achieving a homologous recombination frequency ratio of at least 1 homologous recombination event per 40 random insertion events.

29. The in vitro process as claimed in claim 15, wherein the process further comprises achieving a homologous recombination frequency ratio of at least 1 homologous recombination event per 900 random insertion events.

30. The in vitro process as claimed in claim 15, wherein the process further comprises achieving a homologous recombination frequency ratio of at least 1 homologous recombination event per 40 random insertion events.

31. An in vitro process for providing a recombinant DNA sequence, wherein the process comprises:
  (A) providing a mammalian cell having a recipient DNA sequence, wherein said recipient DNA sequence comprises complementing DNA comprising a first nucleotide sequence and a second nucleotide sequence downstream of said first nucleotide sequence;
  (B) transfecting said mammalian cell in vitro with a transfection DNA comprising:
    (1) a third nucleotide sequence homologous to said first nucleotide sequence;
    (2) a fourth nucleotide sequence homologous to said second nucleotide sequence; and
    (3) a DNA sequence heterologous with respect to said recipient DNA sequence, wherein said heterologous DNA sequence is between said third and said fourth nucleotide sequences and said heterologous DNA sequence comprises a first insertion DNA sequence and a second insertion DNA sequence, wherein said first insertion DNA sequence comprises a regulatory sequence, and said second insertion DNA sequence comprises a coding sequence that encodes a product that confers resistance to a selection agent involved in the selection of transformants, and a promoter allowing the expression of said product in said mammalian cell;
  (C) selecting a transfected cell in which said heterologous DNA sequence has been inserted between said first and said second nucleotide sequences in said recipient DNA sequence by homologous recombination with said third and said fourth nucleotide sequences to thereby provide a mammalian cell containing the recombinant DNA sequence, and in addition, the second insertion DNA sequence encoding the selective agent; and
  (D) recovering said recombinant DNA sequence from said mammalian cell.

32. The in vitro process as claimed in claim 31, wherein said regulatory sequence is a promoter.

33. The in vitro process as claimed in claim 31, wherein said regulatory sequence is an enhancer.

34. The in vitro process as claimed in claim 31, wherein insertion of said heterologous DNA sequence in said recipient DNA sequence is accompanied by replacement of recipient DNA sequence DNA.

35. The in vitro process as claimed in claim 31, wherein each of said third and said fourth nucleotide sequences has a length greater than 150 base pairs and shorter than the length of said recipient DNA sequence.

36. The in vitro process as claimed in claim 31, wherein said recipient DNA sequence is present in said mammalian cell in at least two copies and said heterologous DNA sequence is inserted into only one copy of said recipient DNA sequence.

37. The in vitro process as claimed in claim 31, wherein said mammalian cell is a mouse embryonic stem (E. S.) cell.

38. The in vitro process as claimed in claim 31, wherein said transfection is by electroporation.

39. The in vitro process as claimed in claim 31, wherein the selective agent is neomycin.

40. The in vitro process as claimed in claim 31, wherein said second insertion DNA sequence lacks a polyadenylation sequence and is operably linked at the 3' end to a 5' region of an intron containing a sequence that causes the selective degradation of transcripts of said heterologous DNA sequence.

41. The in vitro process as claimed in claim 31, wherein the process further comprises achieving a homologous recombination frequency ratio of at least 1 homologous recombination event per 900 random insertion events.

42. The in vitro process as claimed in claim 31, wherein the process further comprises achieving a homologous recombination frequency ratio of at least 1 homologous recombination event per 40 random insertion events.

43. The in vitro process as claimed in claim 31, wherein the process further comprises achieving a homologous recombination frequency ratio of at least 1 homologous recombination event per 900 random insertion events.

44. The in vitro process as claimed in claim 31, wherein the process further comprises achieving a homologous recombination frequency ratio of at least 1 homologous recombination event per 40 random insertion events.

* * * * *

UNITED STATES PATENT AND TRADEMARK OFFICE
CERTIFICATE OF CORRECTION

PATENT NO. : 6,638,768 B1
DATED : October 28, 2003
INVENTOR(S) : Herve Mouellic et al.

It is certified that error appears in the above-identified patent and that said Letters Patent is hereby corrected as shown below:

<u>Title page,</u>
Item [57], ABSTRACT, delete in its entirety and substitute therefor:

--There is provided a nucleic acid obtained from the homologous recombination between a heterologous insertion DNA and a recipient gene in a eukaryotic cell, where the function of the insertion DNA or recipient gene is enhanced as a result of the homologous recombination. The nucleic acid includes an insertion DNA, which is heterologous with respect to the recipient gene, and a recipient gene, which comprises a first nucleotide sequence and a second nucleotide sequence downstream of the first nucleotide sequence. The insertion DNA is inserted between the first and second nucleotide sequences in the recipient gene by homologous recombination. The homologous recombination occurs by transformation of a eukaryotic cell comprising the recipient gene with a vector comprising a third and a fourth nucleotide sequence, which are homologous to the first and second nucleotide sequences in the recipient gene, respectively, and the insertion DNA, which is located between the third and fourth nucleotide sequences and does not encode a selection marker involved in the selection of homologous recombinants. Also provided is a process for preparing a nucleic acid by homologous recombination between a heterologous insertion DNA and a recipient gene in a eukaryotic cell, where the function of the insertion DNA or recipient gene is enhanced as a result of the homologous recombination.--.

Signed and Sealed this

Second Day of March, 2004

JON W. DUDAS
*Acting Director of the United States Patent and Trademark Office*